United States Patent [19]
Bron

[11] Patent Number: 6,164,321
[45] Date of Patent: Dec. 26, 2000

[54] LIQUID FLOW REGULATOR FOR USE IN INFUSION SETS

[76] Inventor: Dan Bron, Soroka Street 39/47, 34759 Haifa, Israel

[21] Appl. No.: 09/230,344
[22] PCT Filed: Jul. 23, 1997
[86] PCT No.: PCT/IL97/00250
§ 371 Date: Mar. 18, 1999
§ 102(e) Date: Mar. 18, 1999
[87] PCT Pub. No.: WO98/03216
PCT Pub. Date: Jan. 29, 1998

[30] Foreign Application Priority Data

Jul. 24, 1996 [IL] Israel .......................................... 118933

[51] Int. Cl.$^7$ ...................................................... G05D 7/01
[52] U.S. Cl. .............................................................. 137/501
[58] Field of Search ..................................... 137/501, 517

[56] References Cited

U.S. PATENT DOCUMENTS 3,886,968  6/1975  Murrell ................................... 137/501

*Primary Examiner*—Stephen M. Hepperle
*Attorney, Agent, or Firm*—Larson & Taylor, PLC

[57] ABSTRACT

There is provided a liquid flow regulator, having a split housing (2) including an upper portion (4) connectable to a source of liquid to be dispensed, the upper portion having an inlet port (10) and a lower portion engaging the upper portion and having a control output port leading to the consumer of the liquid, an elastically deformable diaphragm (32) disposed in the housing (2) and defining with a bottom surface of the upper housing portion a first chamber (34), and with a bottom surface of the lower housing portion in which the output control port (24) is made, an output control chamber (36), and a tubular flow attenuator (42) disposed in the housing (2), forming a liquid flow path between the first chamber (34) and the control chamber (36), characterized in that the thickness of the diaphragm (32) is at least equal to the distance between the diaphragm (32) in its state of rest and the output control port (24).

3 Claims, 1 Drawing Sheet

LIQUID FLOW REGULATOR FOR USE IN INFUSION SETS

BACKGROUND OF THE INVENTION

The present invention relates to a liquid flow regulator. In particular, the present invention is suitable for use as an adjustable-rate flow regulator utilizable in an infusion set.

WO 96/03166 (Baxter) discloses a fluid flow regulator provided with a housing and a flexible diaphragm clamped in the housing along its periphery, prebiased so that in its state of rest it assumes an arcuate shape, prestressing the diaphragm towards the outlet, thereby reducing its sensitivity by causing the diaphragm to lose its elastic properties, especially in the range essential for improved control sensitivity required for low rate flows such as those normally used for intravenous administration of fluids.

In U.S. Pat. No. 5,421,363, there is described an adjustable- rate flow regulator with a greatly enhanced accuracy and improved repeatability, over similar prior art flow regulators. This flow regulator is suitable to operate at low dripping rates reaching, for example, 2 ml/hr, at a low pressure drop across the diaphragm of e.,g., only 40 cm of water, in view of a restricted pressure head. The regulator functions as a negative feedback closed loop control system. Due to the relatively long flow attenuating passageway associated with the feedback portion of the system, as well as due to other time constants of the system during operation, the latter tends to become inaccurate, instable and to oscillate vigorously about its set operating flow rate.

SUMMARY OF THE INVENTION

It is therefore a broad object of the present invention to overcome the shortcomings of the above-described and other prior art flow regulators and to provide a flow regulator having improved control sensitivity.

It is a further object of the present invention to provide a flow regulator having improved output flow stability.

In accordance with the present invention there is therefore provided a liquid flow regulator, comprising a split housing including an upper portion connectable to a source of liquid to be dispensed, said upper portion having an inlet port and a lower portion engaging said upper portion and having a control output port leading to the consumer of the liquid, an elastically deformable diaphragm disposed in said housing and defining with a bottom surface of said upper housing portion a first chamber, and with a top surface of said lower housing portion in which said output control port is made, an output control chamber, and a tubular flow attenuator disposed in said housing, forming a liquid flow path between said first chamber and said control chamber, characterized in that the thickness of said diaphragm is at least equal to its working, amplitude being defined by the distance between said diaphram in its state of rest and said output control port.

In a preferred embodiment, the invention further provides a liquid flow regulator, characterized in that said regulator is an adjustable rate regulator, said upper and lower housing portions being rotatably engaged with each other, said tubular attenuator is rotatably engaged with one of said housing portions but non-rotatable relative to the other portion, wherein the inner wall surface of said tubular attenuator defines in conjunction with a housing portion a system of flow-attenuating ducts of said liquid, the flow-attenuating effect of which ducts can be varied to adjust the rate of flow of said liquid.

The invention will now be described in connection with certain preferred embodiments with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

DESCRIPTION OF THE PREFERRED EMBODIMENT

Figure 1:
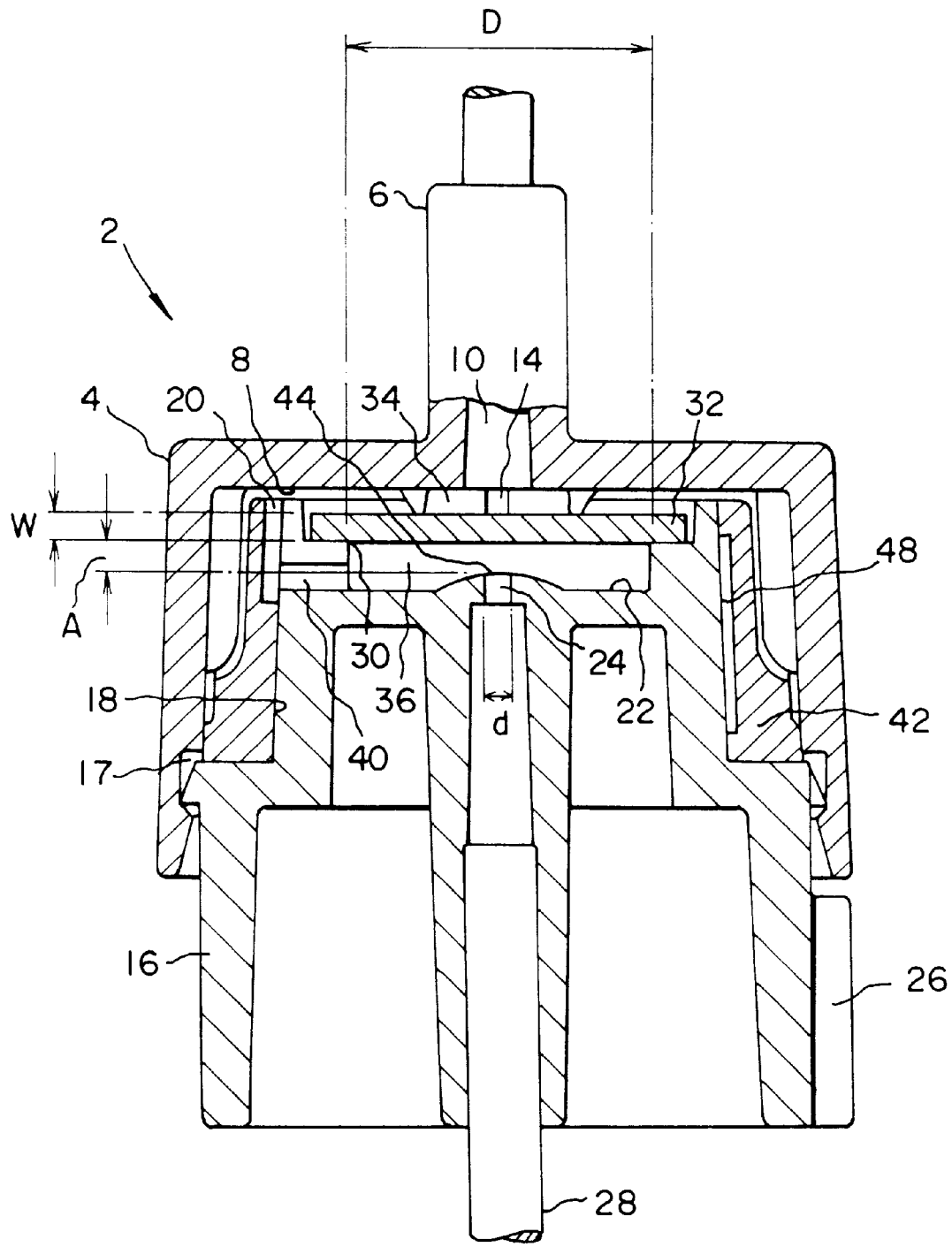
FIG. 1 is a partial cross-sectional view of a flow regulator according to a preferred embodiment of the present invention.

There is shown in FIG. 1 a flow regulator of the present invention, whether of the inline type or of the type adapted to be connectable to a liquid flow line or connectable to an infusion liquid bag or bottle by means of a pointed snout or the like (not shown). The flow regulator shown is advantageously of an adjustable-rate type, however, as will readily be understood hereinafter, the present invention is not limited to adjustable- rate regulators and could be applied to constant-rate flow regulators just as well.

Seen in the Figure is a split housing 2 having an inverted-cup-shaped upper half 4 and connectable to an infusion-liquid bag or bottle (not shown) by means of a conduit 6.

The downward-facing bottom surface 8 of the upper half 4 is provided with an inlet port 10 surrounded by a rim which, at at least one point, has a slot or notch 14, to enable venting of air from a drip chamber when the system is used in conjunction with an infusion set or the like. Hence, the air will be vented via the first chamber and the inlet port into the source of liquid.

The lower housing portion 16 of the split housing 2 snap-locks into an appropriately shaped groove 17 in the substantially cylindrical wall of the upper portion 4 and has one degree of freedom in rotation relative to that of upper portion 4. The lower portion 16 has a neck portion 18 of a reduced diameter and a stepped recess 20 in its upper face. The bottom 22 of the recess 20 is provided with a slightly raised control port 24 of a diameter d.

The lower part of the lower housing portion 16 is seen to carry at least one rib 26 which serves as an index marker to read off the degree of relative rotation (for an adjustable-rate regulator) on a scale (not shown) provided on the upper portion 4. The control port 24 leads to the outside of the housing lower portion 16 via a tubing 28.

Freely seated on a step 30 in the above-mentioned recess 20, there is seen an elastically deformable diaphragm 32 having a thickness W which, with the bottom surface 8 of the upper housing portion 4 defines a first chamber 34, and with the bottom 22 of the recess 20, a second, output control chamber 36. Liquid access to the output control chamber 36 is through a passage 40.

A tubular flow attenuator 42 is positioned by a sliding fit on the neck portion 18 of the lower housing portion 16. The tubular flow attenuator 42 defines in conjunction with housing portion 16 the system of flow attenuating ducts 48 of the liquid. The attenuator 42 is advantageously made of an elastomer. Further details concerning the flow attenuator 42 and the manner of its operation are described in U.S. Pat. No. 5,421,363 and the teaching thereof is herein incorporated by reference.

In order to improve sensitivity and stability and reduce vibrations of the diaphragm 32 during operation, thereby causing deviations and oscillations in the output flow of the regulator, the diaphragms width W should be equal to, or greater than, the working amplitude A of the diaphragm 32 in the output control chamber 36. This amplitude A is substantially the distance between the bottom surface of the diaphragm 32 at rest and a rim 44 surrounding the output control port 24.

A further improvement in the stability of the output flow and in the sensitivity of regulation or control is achieved when the effective or working diameter D of the diaphgram 32, is equal to, or greater than, 20 times the diameter d of the output control port 24.

Also, while in the embodiment shown the attenuator is made with a groove forming labyrinth, such a groove can just well be made in one of the housing portions defining in conjunction with the attenuator a flow-attenuator passageway.

It will be evident to those skilled in the art that the invention is not limited to the details of the foregoing illustrated embodiments and that the present invention may be embodied in other specific forms without departing from the spirit or essential attributes therefore. The present embodiments are therefore to be considered in all respects as illustrative and not restrictive, the scope of then invention being indicated by the appended claims rather than by the foregoing description, and all changes which come within the meaning and range of equivalency of the claims are therefore intended to be embraced therein.

What is claimed is:

1. A liquid flow regulator, comprising:

a split housing including an upper portion connectable to a source of liquid to be dispensed, said upper portion having an inlet port and a lower portion engaging said upper portion and having a control output port leading to a consumer of the liquid; and an elastically deformable diaphragm freely seated in a recess in said lower portion of said housing and defining with a bottom surface of said upper housing portion a first chamber, and with a top surface of said lower housing portion in which said output control port is made, an output control chamber, and a tubular flow attenuator disposed in said housing, forming a liquid flow path between said first chamber and said control chamber, thickness of said diaphragm being at least equal to a working amplitude thereof, the working amplitude being defined by distance between said diaphragm in a state of rest and said output control port.

2. The liquid flow regulator as claimed in claim 1, wherein a working diameter of said diaphragm is at least equal to twenty times the diameter of said control output port.

3. The liquid flow regulator as claimed in claim 1, wherein said regulator comprises an adjustable rate regulator, said upper and lower housing portions being rotatably engaged with each other, said tubular attenuator being rotatably engaged with one of said housing portions but non-rotatable relative to the other portion, an inner wall surface of said tubular attenuator defining in conjunction with a housing portion a system of flow-attenuating ducts of said liquid, the flow-attenuating effect of said ducts being variable to adjust the rate of flow of said liquid.

* * * * *